(12) United States Patent
Ding et al.

(10) Patent No.: US 6,361,801 B1
(45) Date of Patent: Mar. 26, 2002

(54) ALKYL ALLYL AMINES AND LOW VOC HAIR STYLING COMPOSITIONS USING SAME

(75) Inventors: Hong Ding, Darien, IL (US); Michael M. Carpenter, Moon Township, PA (US); Shih-ruey T. Chen, Pittsburgh, PA (US); Nicholas F. Vozza, Burgettstown, PA (US); Fu-Mei Chen Lin; Jennifer R. Parsons, both of Pittsburgh, PA (US)

(73) Assignee: Calgon Corporation, Naperville, IL (US)

( * ) Notice: Subject to any disclaimer, the term of this patent is extended or adjusted under 35 U.S.C. 154(b) by 0 days.

(21) Appl. No.: 09/120,699

(22) Filed: Jul. 22, 1998

(51) Int. Cl.$^7$ ................................................ A61K 7/11
(52) U.S. Cl. ...................... 424/647; 424/45; 424/70.11; 424/70.1; 424/70.17; 424/DIG. 1; 424/DIG. 2
(58) Field of Search ............... 424/45, 46, 47, 424/DIG. 1, DIG. 2, 70.11, 70.1, 70.17

(56) References Cited

U.S. PATENT DOCUMENTS

| | | |
|---|---|---|
| 3,461,163 A | 8/1969 | Boothe |
| 4,348,380 A | 9/1982 | Jacquet et al. |
| 4,946,996 A | 8/1990 | Schleinzer et al. |
| 4,960,588 A | 10/1990 | Hoshowski et al. |
| 5,077,040 A | 12/1991 | Bergmann et al. |
| 5,176,898 A | 1/1993 | Goldberg et al. |
| 5,200,542 A | 4/1993 | Sivak et al. |
| 5,206,009 A | 4/1993 | Watling et al. |
| 5,239,030 A | 8/1993 | Sivak et al. |
| 5,248,737 A | 9/1993 | Sivak et al. |
| 5,435,993 A | 7/1995 | Hamilton et al. |
| 5,458,871 A | 10/1995 | Malawer et al. |
| 5,472,689 A | 12/1995 | Ito |
| 5,501,851 A | 3/1996 | Mudge et al. |
| 5,597,551 A | 1/1997 | Malawer et al. |
| 5,599,524 A | 2/1997 | Morawsky et al. |
| 5,603,919 A | 2/1997 | Liv et al. |
| 5,614,173 A | 3/1997 | Ulmer et al. |
| 5,620,683 A | 4/1997 | Tong et al. |
| 5,626,835 A | 5/1997 | Malawer et al. |
| 5,626,836 A | 5/1997 | Liv et al. |
| 5,637,296 A | 6/1997 | Rocafort |
| 5,658,558 A | 8/1997 | Schwartz |
| 5,686,067 A | 11/1997 | Shih et al. |

FOREIGN PATENT DOCUMENTS

| | | |
|---|---|---|
| EP | 0796087 | 9/1997 |
| GB | 1216399 | 12/1997 |

OTHER PUBLICATIONS

H. Rhee et al., Pd(0)–Catalyzed Coupling Reaction of Allyl N,N–Ditosylimide and Allyl N–Tosylamides as New Substrates for the Formation of π–Allylpalladium Complexes, Bull. Korean Chem. Soc., 19(1), 25–27 (1998).
STN Information Service File: Reg, XP002130512.
STN Information Service File: Reg, XP002130513.
STN Information Service File: Reg, XP002130514.
ROHM & Haas, "The Amazing Amines" Advertisement, 1997.
Rocafort, C. et al., "A New High Performance Hair Fixture Terpolymer Designed For Low Voc Formlation", *Spray Technology & Marketing*, 1998, pp. 30–35.
Vitale, M., "Niche Solutions for 5590 Voc Hair Sprays", *Spray Technology & Marketing*, May, 1998, pp. 36–39.

*Primary Examiner*—Raj Bawa
(74) *Attorney, Agent, or Firm*—Michael B. Martin; Thomas M. Breininger (57) ABSTRACT

The present invention is directed to alkyl allyl amine monomers and their use as a polymerizate in a low VOC hair spray formulation. The hair spray formulation preferably includes a polymerizate of an alkyl allyl amine monomer, preferably an alkyl diallyl amine monomer alone or in combination with other known monomers. The hair spray formulation preferentially satisfies low VOC requirements while maintaining characteristics desired in a hair fixative product.

15 Claims, 4 Drawing Sheets

Conditions:
2 hours @ 95% relative humidity
5% solids, 3 replicates per treatment

ALKYL ALLYL AMINES AND LOW VOC HAIR STYLING COMPOSITIONS USING SAME

FIELD OF THE INVENTION

The present invention relates generally to an alkyl allyl amine, more particularly to a polymer formed from an alkyl allyl amine, and even more particularly the present invention relates to a hair fixative composition utilized in styling gels, mousses or sprays (aerosol or pump) which includes a polymerizate of an alkyl allyl amine. It is preferable that the aqueous hair styling composition of the present invention contain a low concentration of volatile organic compounds (VOCs), with it being preferable that the VOCs make up 80% or less of the overall concentration of the hair spray formulation, and even more preferably that the VOCs make up 55% or less of the overall concentration of the hair spray formulation.

BACKGROUND OF THE INVENTION

Hair fixing or styling formulations are used to hold hair in a particular shape or configuration. They can take the form of, for example, hair sprays (aerosol or pump), styling gels, spray-on gels, or mousses. Hair styling formulations normally form a thin film of hair fixative resin when applied to the hair. This thin film of resin holds adjacent hairs together to retain a particular shape or configuration. When the hair styling composition is formulated as a spray it is most common to use a propellant (i.e. an aerosol) in the hair styling formulation. This normally adds to the overall VOC content of the hair spray formulation.

Hair fixing or styling formulations typically contain one or more volatile organic compound (VOC). VOCs as defined by the Environmental Protection Agency (EPA) contain at least one carbon atom and are typically used as solvents or propellants in the hair styling compositions. VOCs contribute to ground level air pollution in the presence of sunlight and air, and are volatile under ambient conditions. VOCs include, for example, $C_1$ to $C_{12}$ straight or branched chain alcohols such as methanol, ethanol, propanol, isopropanol, or butanol; $C_1$ to $C_{12}$ straight or branched chain hydrocarbons such as methane, ethane, propane, isopropane, isobutane, pentane, isopentane, or butane; or ethers such as dimethyl ether, or dimethoxymethane.

Aerosol hair sprays traditionally were formulated to contain 90–95% VOC in the form of ethanol and hydrocarbon propellants. In April 1996, the EPA published the first nationwide VOC regulations for consumer and commercial products, requiring all hair spray to meet an 80% VOC limit by March 1997. Air pollution issues in heavily populated metropolitan areas such as California are required to have more stringent regulations than the EPA, making these areas the bellwether for mass VOC regulations. The California Air Resources Board has had an 80% VOC limit in effect since 1993 and currently plans to enforce a 55% VOC limit on hair sprays by mid-year 1999. Other states with highly populated areas, such as New York, Connecticut and Texas, have also considered enacting a 55% VOC limit.

The 55% VOC limit is much more of a challenge from a technical perspective than the 80% limit because the addition of large amounts of water to the hair spray formulation negatively affects both the hold performance and spray characteristics of the hair spray. Water impacts hold performance because it contributes to an increase in solution viscosity and surface tension. This results in increased initial curl droop and extends both tack time and dry time. Spray performance is impacted because an increase in viscosity (generally greater than 15 centipoise) of the spray solution leads to coarser, wetter sprays which are inefficient in coating the hair. In addition, the introduction of water causes compatibility problems in the ethanol/hydrocarbon solvent/propellant systems used for hair sprays, and can also lead to corrosion problems in steel cans used as vessels for the hair sprays.

Water can also cause the composition, when sprayed, to form droplets or beads on the hair. These beads leave undesirable visible residue on the hair when dried, and can impart a raspy feel to the hair when combed. Water soluble hair fixative resins, when used in low VOC hair styling formulations, are also more likely to become tacky after being applied to the hair. The water soluble hair fixative resins in a low VOC hair styling formulations may also have poor curl retention properties due to their inability to dry completely when applied to the hair.

These undesirable properties become particularly severe when the hair styling formulation contains 15 weight percent or more water. As a result, hair styling formulators have begun to redesign their hair styling compositions in order to formulate hair styling compositions or hair sprays which achieve low VOC levels, but yet which are acceptable for their intended use. In this regard, hair style formulators have focussed on using solvents which are not classified as VOCs and on developing resins which are suitable in low VOC formulations. A resin is considered suitable when it can be applied to the hair in a carrier at low VOC and form a smooth feeling film and is resistant to cracking or breaking when combed. An example of a low VOC hair styling formulation already developed is U.S. Pat. No. 5,176,898 to Goldberg, et al., which discloses an aqueous hair spray formulation having less than 80 weight percent VOC. The aqueous hair spray formulation contains from 1 to 10 weight percent volatile silicone, preferably cyclomethicone or dimethicone copolyol, from 15 to 40 weight percent water/alcohol solution, from 5 to 60 weight percent propellant, from 1 to 10 weight percent water soluble hair fixative resin, and from 0.05 to 3.0 weight percent neutralizer/plasticizer.

SUMMARY OF THE INVENTION

The present invention is directed to an alkyl allyl monomer and polymers thereof, particularly an alkyl allyl monomers useful in a hairspray formulation. More particularly the present invention is directed to a hair spray formulation which satisfies low VOC standards now in place and those anticipated in the future, and which overcomes a number of undesirable characteristics found in known low VOC hair spray formulations (i.e., decreased hold, increased tackiness, larger particle size, poor spray patterns, increased drying times, instability due to hydrolysis, increased can corrosion and poor compatibility with the solvent.

The present invention is directed to an alkyl allyl amine represented by the formula:

(1)

wherein $R_1$ represents hydrogen or an allyl, $R_2$ represents hydrogen or methyl, n is an integer from 0 to 6, $R_4$, $R_5$ and $R_6$ each independently represent a hydrogen atom, an alkyl group having from 1 to 22 carbon atoms, a cycloalkyl group having 3 to 22 carbon atoms, a cycloalkylene (i.e. an aryl group) having 6 to 22 carbon atoms or an alkylaryl group having from 7 to 22 carbon atoms.

It is preferable that at least one of $R_4$, $R_5$ or $R_6$ represent a substituent other than hydrogen, and more preferable that the alkyl portion of the alkyl allyl amine represented in formula (2) below be a branched alkyl group, more preferably, a tertiary alkyl group, more preferably a tertiary butyl group, and most preferably a tertiary octyl group:

(2)

The alkyl group may also include methylene spacers ($n \geq 1$) before the alkyl group begins to branch. The alkyl group may also include a hetero atom or a functional group. It is preferable that the alkyl allyl amine be a tertiary octyl mono allyl amine represented by formula (3) below:

(3)

wherein $R_2$ represents hydrogen or methyl.

There appears to be a beneficial effect when the alkyl allyl amines of the present invention are symmetrical. It is speculated that the benefit is due to a more rigid polymer structure. Thus, it is more preferable that $R_1$ of Formula (1) represent an allyl group, with $R_2$ and $R_3$ each independently representing a hydrogen or methyl group, with it being most preferred that $R_2$ and $R_3$ be the same, and even more preferred that both $R_2$ and $R_3$ both be hydrogen. Formula (4) below illustrates a preferred alkyl diallyl amine which has a substantial degree of "symmetry":

(4)

wherein $R_2$ and $R_3$ each independently represent hydrogen or methyl, n is an integer from 0 to 6, $R_4$, $R_5$ and $R_6$ each independently represent a hydrogen atom, an alkyl group having from 1 to 22 carbon atoms, a cycloalkyl group having from 3 to 22 carbon atoms, a cycloalkylene (i.e. an aryl group) having from 6 to 22 carbon atoms or an alkylaryl group having from 7 to 22 carbon atoms.

As with the alkyl mono allyl amine, it is also preferred that the alkyl portion of the diallyl amine be a branched alkyl group, more preferably a tertiary group (see Formula (2)) such as a tertiary butyl group, and even more preferred that it be a tertiary octyl group. Such a preferred embodiment, for instance, t-octyl diallyl amine (TODA), may be represented by the formula:

(5)

The present invention also relates to a hair fixative resin comprised of a polymer formed from an alkyl allyl amine monomer. The alkyl allyl amine monomer may be either a alkyl diallyl amine (i.e. formula (4)) or an alkyl mono allyl amine (i.e. formula (1) wherein $R_1$ is hydrogen). The polymer may be generally represented by the formula:

$$[L]_x\text{---}[M]_y\text{---}[N]_z \qquad (6)$$

where x, y and z are integers equal to or greater than 1 and a sum of x, y and z is an integer greater than 5, and where L, M and N represent a conversion unit of a monomer which may be the same or different from each other. L, M, and Z may be random or repeating sequences of a conversion unit of a monomer with at least one of L, M and N being a conversion unit of an alkyl mono allyl amine (i.e. the polymerizate of formula (1) wherein $R_1$ is H) or a conversion unit of alkyl diallyl amine of formula (7) shown below:

(7)

wherein $R_2$ and $R_3$ each independently represent hydrogen or methyl, l is 0 or 1, if l is 0, m is 1, and if l is 1, m is 0, n is 0 to 6, and $R_4$, $R_5$ and $R_6$ each independently represent hydrogen, an alkyl group having from 1 to 22 carbon atoms, a cycloalkyl group having from 3 to 22 carbon atoms, a cycloalkene (i.e. an aryl group) having from 6 to 22 carbon atoms or an alkylaryl group having from 7 to 22 carbon atoms.

It is preferable that the polymer be formed as a homopolymer, that is, where L, M and N are all the conversion product of either the alkyl allyl amine monomer of formula (3), the conversion product of the alkyl diallyl amine of formula (5) (i.e. that of formula (7)), or a conversion unit of another known monomer. In the where L, M and N are different, the conversion units appear in a regular sequence. Even more preferably the polymer is a copolymer formed from, for example a monomer of Formula (5) and Formula (3), a methyl methacrylate monomer, or acrylic acid monomer or a combination thereof, For example, L, M and N of formula (6) may be a conversion unit of any (meth)acrylate or (meth)acrylic acid (i.e., methyl methacrylate, acrylic acid) as well as an alkyl diallyl amine or alkyl mono allyl amine in a regular or random sequence. Other monomers which may be used in conjunction with either the alkyl diallyl amine and/or alkyl mono allyl amine of the present invention include a monomer selected from the group consisting of (meth)acrylates, acrylamides, and (di)allyl ammonium salts. For example, acrylamide, butyl aminoethyl methacrylate, methyl octyl diallyl ammonium bromide, dimethylamino ethylacrylate, tertiary-octyl acrylamide, and isobornyl methacrylate are suitable monomers useful in the present invention.

It is preferable that the polymer of formula (6) include a conversion unit of the alkyl diallyl amine and that the that the alkyl group of the alkyl allyl amine be a branched alkyl group, more preferably a tertiary butyl group, and most preferably a tertiary octyl group. The polymer formed from a tertiary octyl diallyl amine monomer may be represented by formula (8) below:

(8)

wherein each of $R_2$, $R_3$, $R_4$, $R_5$, $R_6$, l, m, n, L, N, x, y and z have the same definition as with regard to formula (6) and (7) above and wherein at least one of $R_4$, $R_5$ and $R_6$ of formula (8) are an alkyl group, even more preferably a t-alkyl group represented by Formula (2) above.

In the most preferred embodiment of the present invention, the polymer is incorporated in a hair spray or fixative formulation comprised of a volatile organic compound at a weight percentage of less than 80%, more preferably a hair spray formulation having a VOC concentration less than 55%. Typically, the hair spray formulation includes water and/pr other exempt solvents. The hair spray formulation preferably includes a VOC selected from the group consisting of methanol, an alcohol (i.e., ethanol, propanol, isopropanol, butanol) dimethoxymethane, and dimethyl ether. The hair spray formulation may also include acetone, typically classified as a solvent exempt from the VOC category as well as other solvents exempt from the VOC classification. It is preferable that the hair fixative formulation be formed at least in part with the monomer of formula (1), more preferably from a monomer wherein $R_1$ of formula (1) is an allyl group and the alkyl portion of formula (1) is tertiary alkyl, more preferably t-octyl as shown in formula (4) above.

The present invention is also directed to a method of manufacturing a hair fixative comprised of polymerizing an alkyl allyl monomer either as a homopolymer or a copolymer preferably along with methyl methacrylate and/or acrylic acid monomer. It is preferable that water and carrier solvents, including VOC solvents are mixed with the polymer and that, the overall concentration of VOCs in the hair spray formulation are less than 80% (wt/wt %) and more preferably less than 55% (wt/wt %) or less VOC.

The features, aspects and advantages of the present invention will become better understood with regard to the following description, appended claims, and accompanying drawings where:

DETAILED DESCRIPTION OF THE PRESENT INVENTION

The present invention is directed to a series of alkyl allyl amines useful as polymerizates in low VOC hair styling formulations. The alkyl allyl amines are prepared in accordance with the following formula:

(9)

wherein $R_7$ is equivalent to $R_2$ and/or $R_3$ as defined elsewhere herein and represents hydrogen or methyl, n is an integer from 0 to 6, $R_8$ represents a suitable leaving group, preferably a halide, more preferably a halide selected from the group consisting of chloride and bromide, most preferably bromide, $R_4$, $R_5$ and $R_6$ each independently represent a hydrogen atom or an alkyl group having from 1 to 22 carbon atoms and wherein $R_4$, $R_5$, and $R_6$ may also represent a cycloalkyl group having from 3 to 22 carbon atoms, a cycloalkylene (i.e. an aryl group) having from 6 to 22 carbon atoms or an alkylaryl group having from 7 to 22 carbon atoms. It is preferable that $R_4$, $R_5$ and $R_6$ do not represent hydrogen at the same time. In other words, it is preferable that the alkyl portion of the alkyl allyl amine be branched and more preferably a tertiary alkyl group.

The ratios of alkyl mono allyl amine to alkyl diallyl amine synthesized and to some degree the amount of byproduct may be controlled by varying experimental conditions such Using the general synthesis techniques described above, a number of alkyl mono allyl amines and alkyl diallyl amines are synthesized and tested for their suitability in low VOC hair spray formulations.

These include the following alkyl ally amines:

TABLE 1

| Name | Chemical Formula | Abbrev. |
|---|---|---|
| tertiary octyl mono allyl amine | $H_2C=CHCH_2NHC(CH_3)_2CH_2C(CH_3)_3$ | TOMA |
| tertiary octyl diallyl amine | $(H_2C=CHCH_2)_2NC(CH_3)_2CH_2C(CH_3)_3$ | TODA |
| octadecyl mono allyl amine | $H_2C=CHCH_2NH(CH_2)_{17}CH_3$ | OCMA |
| octadecyl diallyl amine | $(H_2C=CHCH_2)_2N(CH_2)_{17}CH_3$ | OCDA |
| oleyl mono allyl amine | $H_2C=CHCH_2NH(CH_2)_8HC=CH(CH_2)_7CH_3$ | OLMA |
| oleyl diallyl amine | $(H_2C=CHCH_2)_2N(CH_2)_8HC=CH(CH_2)_7CH_8$ | OLDA |
| docosyl mono allyl amine | $H_2C=CHCH_2NH(CH_2)_{21}CH_3$ | DOMA |
| docosyl diallyl amine | $(H_2C=CHCH_2)_2N(CH_2)_{21}CH_3$ | DODA | as mole concentration of reaction substrates (i.e. allyl chloride) to the alkyl amine. For example, if it is desirable to increase the ratio of alkyl diallyl amine to alkyl monoallyl amine, an increase in molar concentration is preferred. To obtain a higher concentration of diallyl to mono allyl product, it is preferable that the allyl halide be in the range of about 1.5 to about 2.5 times the mole concentration of alkyl amine, and more preferably about 2 times the mole concentration of the alkyl amine. For purposes herein, the term "about" means plus or minus ten percent (10%) of the number at issue (i.e., "about 10" means in the range of 9–11). It has also been found that it is preferential to use allyl chloride when forming the mono allyl amine product and allyl bromide (both allyl chloride and allyl bromide are available from the Aldrich Chemical Company of St. Louis; Mo.) when forming the diallyl amine product. A typical synthesis of mono-allyl amine occurs as follows.

In a round bottom glass equipped with a condenser and stirrer, t-octylamine (1,1,3,3 tetramethyl butyl amine) available from Aldrich is added at a mole concentration of 0.95 mole (129.25 g available at 95% purity) and 2.3 mole of 50% NaOH (184.0 g). Added to this combination is allyl chloride at a mole concentration of 2–5 mole (197.3 g) over one hour at 25° C. The flask is observed for exothermic reaction and at the end of one hour heated to 55° C. and stirred for 40 hours. The resulting product is about 69% t-octyl mono allyl amine, about 30% t-octyl amine and about 10% t-octyl diallyl amine. The reaction product is rotovapped resulting in a final reaction product of about 71% t-octyl mono-allyl amine, 27% t-octylamine, and 1.5% by-product, This product is then purified using flash liquid chromatography.

To obtain the alkyl diallyl amine of the present invention, 0.95 moles of t-octyl amine, 2.3 moles of NaOH (50%) and an excess of allyl chloride (2.5 moles) are mixed in a reaction flask. The reaction flask is kept at 15 psi and 85° C. while stirring for 8 hours. The temperature is then increased to 100° C. for an additional 8 hours. This results in about 10% t-octyl diallyl amine, about 82% t-octyl mono allyl amine, and about 8% t-octyl amine. The pressure is adjusted to 1 atm and 1 mole of allyl bromide is added to a 2 liter reaction vessel which is then heated at 85° C. for an additional 12 hours. The resulting reaction product is comprised of about 88% t-octyl diallyl amine, about 2.2% mono allyl amine and about 8.8% by-product. The t-octyl diallyl amine is then purified via flash chromatography.

From these alkyl amines it was determined that the most suitable formulations were those having branch alkyl groups, and more preferably those classified as alkyl diallyl amines, even more preferably, branched alkyl diallyl amines, and most preferably tertiary alkyl diallyl amines. In addition to the abbreviations above, the following monomers and their corresponding abbreviations may be used herein: acrylic acid ("AA"); acrylamide ("AM"); methyl methacrylate ("MMA"); butyl aminoethyl methacrylate ("BAEMA"); methyl octyl diallyl ammonium bromide ("MODAAB"); dimethylamine ethylacrylate ("DMAFA"); and tertiary-octyl acrylamide ("TOAM").

In order to determine the suitability of the alkyl allyl amines of the present invention, a slightly modified Personal Care Application Test Procedure, PC-006, for curl retention of aqueous polymer solutions was used. The modifications included an abbreviated washing procedure and different application of the test solution since hair sprays traditionally are not rinsed off the hair prior to setting. The hair tress for hair setting resin evaluation utilized 2 grams of 8" dark brown European virgin hair on a top loading balance. A layer of hot glue was applied to one side of a 2" piece of wood cut from a tongue depressor and the root end of the hair was placed on the hot glue with approximately 0.25" of the root and extending over the top edge of the wood. The hair was arranged so that it was evenly distributed across a one-inch area within the center of the piece of wood. A second layer of hot glue was placed over the hair in contact with the wood. Then, a second identical piece of wood was placed over the glue so that the root end of the hair was securely sandwiched between the two pieces of tongue depressor. The glue was allowed to dry a few minutes and the root ends of the hair was trimmed so that it was flush with the wood.

The hair tress prepared as above was immersed in 15% Triton X-100 (octylphenoxy polyethoxyethanol nonionic surfactant, raw material code OM-JJ21-00) solution for 2 minutes to wash it. The hair tress was rinsed for 2 minutes under running de-ionized water. The hair tress was immersed and then rinsed in 1% (by weight) aqueous sodium chloride solution (1 hour immersion for 2 minutes) and then rinsed with de-ionized water. The de-ionized water was changed and the hair tress was soaked in fresh de-ionized water for 3 hours. The de-ionized water was changed again and the hair tress was again soaked in fresh de-ionized water overnight. The hair tress was then removed from the water and allowed to air dry for 24 hours. Once dry, the clean hair tress was placed in a plastic bag and stored flat for future use.

The clean curl retention tree was secured by a stainless steel curl retention clamp and the ends are trimmed to 6" length using a sharp paper cutter. The trimmed hair was detangled utilizing the wide end of a comb and then combed with the fine end of the comb twice. The tress was immersed in 100 mL of hair setting solution for 10 seconds. Any excess solution was removed by running the hair tress between the fingers twice. The hair was then detangled and combed twice with the fine end of the comb. Starting with the hair at the left edge of the roller, the hair was wound onto the roller ending its wind on the right-hand edge of the roller. The curled hair was secured with a clip. The rolled tresses were hung on the curl retention board (a peg board marked with gradations for measuring the length of the curl) and conditioned at 50% relative humidity overnight. The next day about 600 mL de-ionized water was added to each of two glass dishes in a humidity chamber. Sodium sulfite was poured into each dish to cover the bottom, making a saturated solution that allowed the chamber to achieve 95% relative humidity. Once the chamber reached 95% relative humidity, each clamp was pulled to the front of the peg to keep the tress from touching the board. Or is to be noted that at this point, the curl retention board with the tresses was still outside of the humidity chamber. Each of the tresses are unwound are at a time into a helical configuration, and the initial length ($L_0$) is recorded. Working quickly to avoid loss of humidity, the rack of curls was placed into the humidity chamber and a timer was set for 15 minutes. At 15 minute intervals for a total of 2 hours, the length of each curl ($L_1$) was measured. Subsequent timings were studied at the beginning of recording the length of the first tress. The temperature and relative humidity at each interval was to calculate % Curl Retention (% CR) equation 1 was used:

$$\% \, CR = \frac{(L - L_1)}{(L - L_0)} \times 100 \quad (1)$$

For initial test development, five competitive resins targeted for 55% VOC hair spray formulations were evaluated using the prototype formulations recommended in the literature, excluding any additives extraneous to the basic ingredients of water, ethanol, resin and neutralizer. The competitive resins utilized were as follows, listed by Resin Name, (Manufacturer) and—Description: Acudyne 255 (Rohm & Haas)—acrylates/hydroxyesters acrylated copolymer; Amerhold DR 25 (Amerchol)—acrylates copolymer; Amphomer LV 71 (National Starch & Chemical)—octylacrylamide acrylateslbutylaminoethyl methacrylate copolymer; Eastman AQ 48 (Eastman Chemical)—diglycol CHDA/isophthalates/SIP copolymer; Lovocryl 47 (National Starch $R_6$ Chemical)—octylacrylamide acrylates/butylaminoethyl methacrylic acid; Omnirez 2000 (ISP); and Resyn 28-2930 (National Starch & Chemical)—VA/crotonates/vinyl neodecanoate copolymer. These standars were utilized to evaluate the effectiveness of alkyl allyl amines of the present inention of various VOC levels Instead of immersing the hair these tresses were treated with the aerosol by attaching a Bulldog clip to the bottom of each tress to act as a weight and sprayed for five seconds each on the front and back. The poor performance of this sample, which only achieved 45% curl retention after 3 hours is not necessarily an indication of an inferior product, but rather illustrates that the two different methods of applying resin to the hair should not be compared directly and identifies the need to develop a separate test method for testing aerosol products. Examples of tests which may be used to test aerosols are disclosed in Micchelli, A. L. and Koehler, F. T., "Polymer Properties Influencing Curl Retention at High Humidity", *J. Soc. Cosmetic Chemists*, 19, 863–890 (1968); Takada, S., "Possibilities of Improving the Quality of Hair Spray", *Aerosol Report*, 11(172), 12–25 (1972); and Reed, A. B., Jr., and Bronfein, I., "Curl Retention with Hair Sprays", *Drug Cosmet. Ind.*, 94, 178 (1964), the teaching of each of which as it pertains to aerosol testing is specifically incorporated herein by reference thereto.

The polymers studied herein were formulated using polymerization techniques known in the art. Usually polymerization is carried out with a catalyst such as initiators, heat or light (i.e., U.V.) and sometimes under high pressure. In the examples described herein the unsaturated polymerizable monomers were combined by a technique known as addition in which free radicals are the initiating agents that react with the double bond of the monomer by adding to it on one side and at the same time producing a new free electron on the other. By this mechanism the chain becomes self-propagating. Polymerization as described here may also occur by condensation involving the splitting out of water molecules by two reacting monomers and by so-called oxidative coupling. The polymerization techniques described herein can be: (1) in the gas phase at high pressures and temperatures (200° C.); (2) in solution at normal pressure and temperatures from −70° to +70° C.; (3) bulk or batch polymerization at normal pressure at 150° C.; (4) in suspension at normal pressure at 60° to 80° C.; and (5) in emulsion form at normal pressure at —20° to +60° C. (used for copolymers). In addition, catalysts of the peroxide type sometimes are necessary with these methods.

In particular, hair spray formulation samples were prepared with varying levels or ratios of tertiary-octyl diallyl amine monomer (TODA), methyl methacrylate (MMA) and acrylic acid (AA). These samples along with various industry standards were evaluated for solubility, Brookfield Viscosity, film clarity and curl retention to determine their applicability to low VOC hair setting resins. 30/40/30 TODA/AA/MMA, performed especially well with respect to these attributes, particularly solubility, film clarity and curl retention, and had viscosity slightly higher than optimum.

Based on the screening evaluation in solubility, film clarity and curl retention, 30/40/30 TODA/AA/MMA is applicable for hair setting applications, and would be preferred over 40/20/40 TODA/AA/MMA. However, 40/20/40 TODA/AA/MMA (Sample #1) may be more suitable if an exempt VOC solvent such as acetone is utilized. Using the 30/40/30 TODA/AA/MMA composition as a starting point composition and molecular weight were analyzed to achieve optional performance for solubility, Brookfield Viscosity, film clarity and curl retention in 55% VOC hair setting applications.

Samples were evaluated for solubility in three types of water/ethanol solutions, as outlined in Table 2 below. SD-40 ethanol (200 proof) and de-ionized water were used in all formulations.

TABLE 2

| | % Resin Solids | % Ethanol | % De-ionized Water |
|---|---|---|---|
| 80% VOC | 5 | 80 | 15 |
| 55% VOC | 5 | 55 | 40 |
| Aerosol Concentrate | 8 | 30 | 62 |

The aerosol concentrate is the base formulation for a 55% VOC aerosol spray while generally results in 5% resin solids when charged with propellant at 65% concentrate and 35% propellant. The final aerosol formula would contain approximately: 5% resin solids, 20% ethanol, 40% de-ionized water and 35% propellant.

The propellant used in this study was dimethyl ether (DME), which is more compatible with water than hydrocarbons such as isobutane and propane. DME, however, is also classified as a VOC, thus, the 35% DME plus the 20% ethanol combine to account for 55% VOC in this aerosol formula. Aerosol formulations were prepared by weighing the concentrate into a shielded aerosol reaction vessel, sealing with a SeaquistPerfect valve and charging with the required weight of dimethyl ether.

LV 71 at 80% VOC and Eastman AQ 48 at 55% VOC. The Amphomer was also soluble at 55% VOC, but in our preparation required neutralization with AMP-95. The Eastman AQ 48, which is targeted specifically for 55% VOC, was not soluble at 80% VOC. The AQ family of resins from Eastman is designed to be more tolerant of water than ethanol, so this result is expected.

The Brookfield Viscosity's at 30 rpm of the 55% and 80% formulations where the four resins were soluble are summarized in Table 3 below:

TABLE 3

Properties of TODA/AA/MMA Hair Setting Resins
Solubility, Film Clarity and BF Viscosity
(5% solids in hydroalcoholic solutions)

| Sample | Description | Solubility | | | Film Clarity | | BF Viscosity (cps) UL Spindle @ 30 rpm, 25° C. | |
|---|---|---|---|---|---|---|---|---|
| | | 55% Ethanol | 80% Ethanol | Aerosol Concentrate | 55% Ethanol | 80% Ethanol | 55% Ethanol | 80% Ethanol |
| Sample #1 | 40/20/40 TODA/AA/MMA | Y | Y | N | cloudy | mostly cloudy | 3.40 | 2.46 |
| Sample #2 | 30/40/30 TODA/AA/MMA | Y w/neut. | Y w/neut. | Partial w/neut. | clear | clear | 17.3 | 10.6 |
| Amphomer LV 71 | octylacrylamide/ acrylates/ butylaminoethyl methacrylate copolymer | Y w/neut. | Y | — | slightly cloudy | clear | 7.60 | 5.90 |
| Eastman AQ 48 | diglycol/CHDM/i sophthalates/SI P copolymer | Y | N | — | clear | NA | 3.34 | NA |

Brookfield viscosity was measured at 25±1° C. on a Brookfield Viscometer Model DVLV-III equipped with a UL adapter and spindle. Resin samples were evaluated for curl retention at 5% solids according to the method described above. To test film clarity, film was drawn from 55% and 80% VOC solutions on a 25×75 mm plain glass microscope slide, allowed to dry and visually evaluated for clarity.

A number of TODA/AA/MMA polymers synthesized for 55% VOC hair spray application were compared with Amphomer LV 71 and Eastman AQ 48 for solubility, Brookfield Viscosity, film clarity and curl retention.

Sample #1, 40/20/40 TODA/AA/MMA, was soluble at 5% solids in 55% and 80% VOC solutions but somewhat insoluble in the aerosol concentrate at 8% solids and 30% ethanol. Solubility at 55% and 80% VOC was also achieved with Sample #2, the 30/40/30 TODA/AA/MMA composition. This sample was also partially soluble in the aerosol concentrate; however, neutralization with AMP-95 (2-amino-2-methyl-1-propanol), 95% solution (Angus Chemical) was preferred in all the formulations to better solubilize the samples.

The aerosol concentrate is described as only partially soluble because after several hours of stirring there remained a small amount of insoluble material remaining. Since there was such a small amount of this insoluble material, it was filtered off and the remaining supernatant was used to prepare a 55% VOC aerosol formulation with dimethyl ether. This solution remained clear; however, there was evidence of some incompatibility in areas of localized propellant concentration as it was charged to the vessel.

As expected, competitive industry samples were soluble at the VOC levels for which they were targeted, Amphomer As discussed above, a viscosity range of about 15–17 centipoise is an acceptable range, but for aerosol formulations, in particular, 3–4 cps to achieve the preferred spray characteristics in 55% VOC hair spray formulation. The data shows that while both samples achieve acceptable target viscosity range, Sample 1 achieves the preferred target viscosity range for aerosols and thus is preferable over Sample 2. The molecular weight of Sample 2 was targeted to be higher than that of Sample 1 which probably contributed to the higher viscosity. The viscosity of Eastman AQ 48 was in the optimal range of 3–4 at 55% VOC. This would be as expected since the resin was commercialized to meet the 55% VOC requirements. Amphomer LV 71 has a viscosity higher than that of Eastman AQ 48 at 55% VOC; however, Amphomer is touted primarily for 80% VOC formulations instead of 55% VOC. Note that the 80% VOC formulations all had lower viscosities than the 55% VOC formulations. This was also be expected since 55% ethanol in water has higher viscosity than 80% ethanol in water without any resin present. This phenomenon highlights the challenge of achieving the desired low viscosity, especially for existing resins like Amphomer LV 71 which perform well at 80% and higher VOC, but cannot achieve the required spray characteristics at 55% VOC.

Table 3 also highlights the clarity of films formed by 55% and 80% VOC formulations of the four resins. Sample #1 formed cloudy films at both 55% and 80% VOC. By changing the composition from 40/20/40 TODA/AA/MMA, Sample #2, film clarity was achieved at both 55% and 80% VOC. Amphomer LV 71 formed a clear film at 80% VOC, however, at 55% VOC the Elm was slightly cloudy. As expected, Eastman AQ 48 formed a clear film at 55% VOC.

Figure 1:
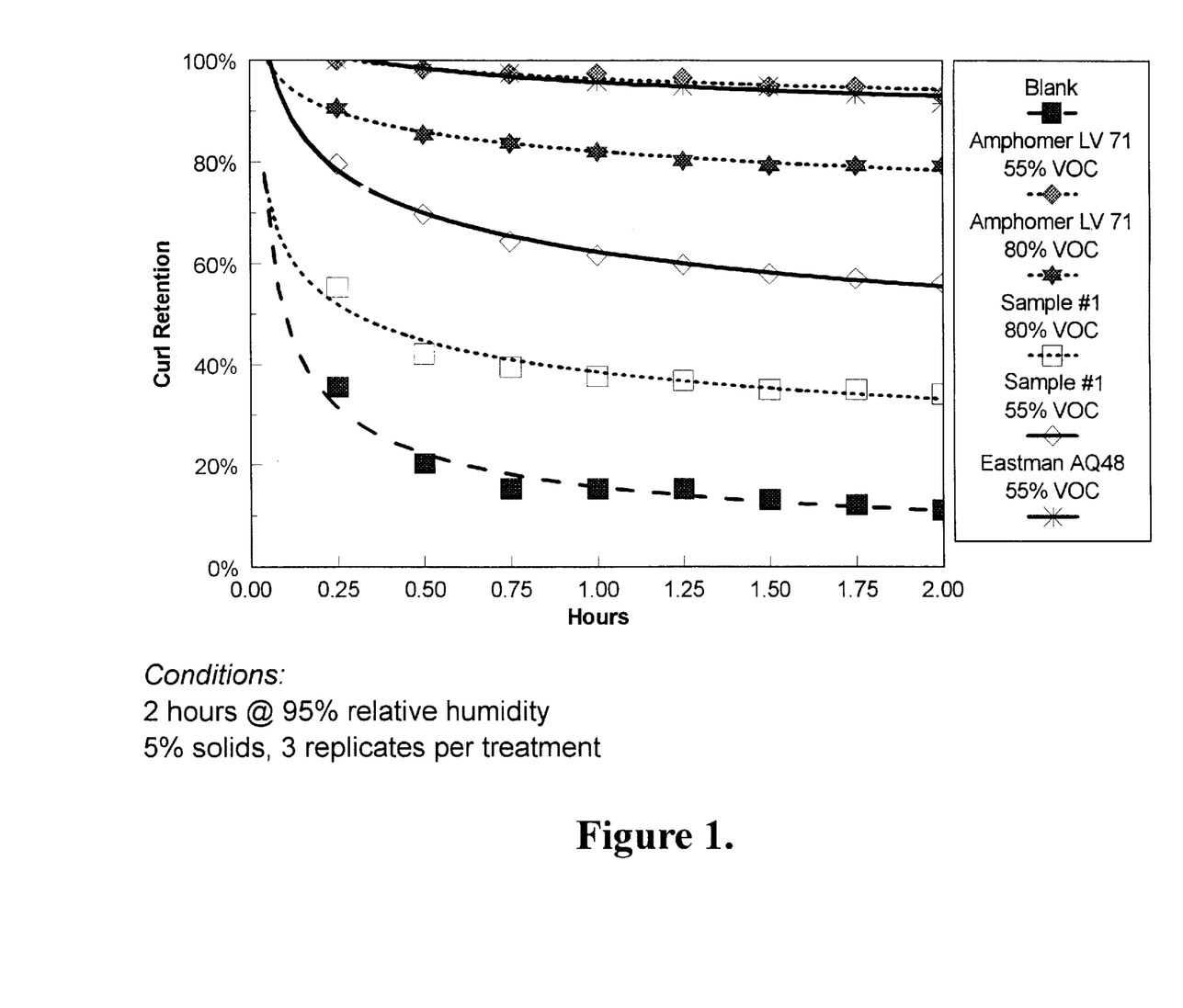
FIG. 1 illustrates curl retention of TODA-based resins (Sample #1—40/20/40 TODA/AA/MMA) in a low VOC hair spray formulations when compared to industry standards Amphoner LV71 and Eastman AQ48.
Figure 2:
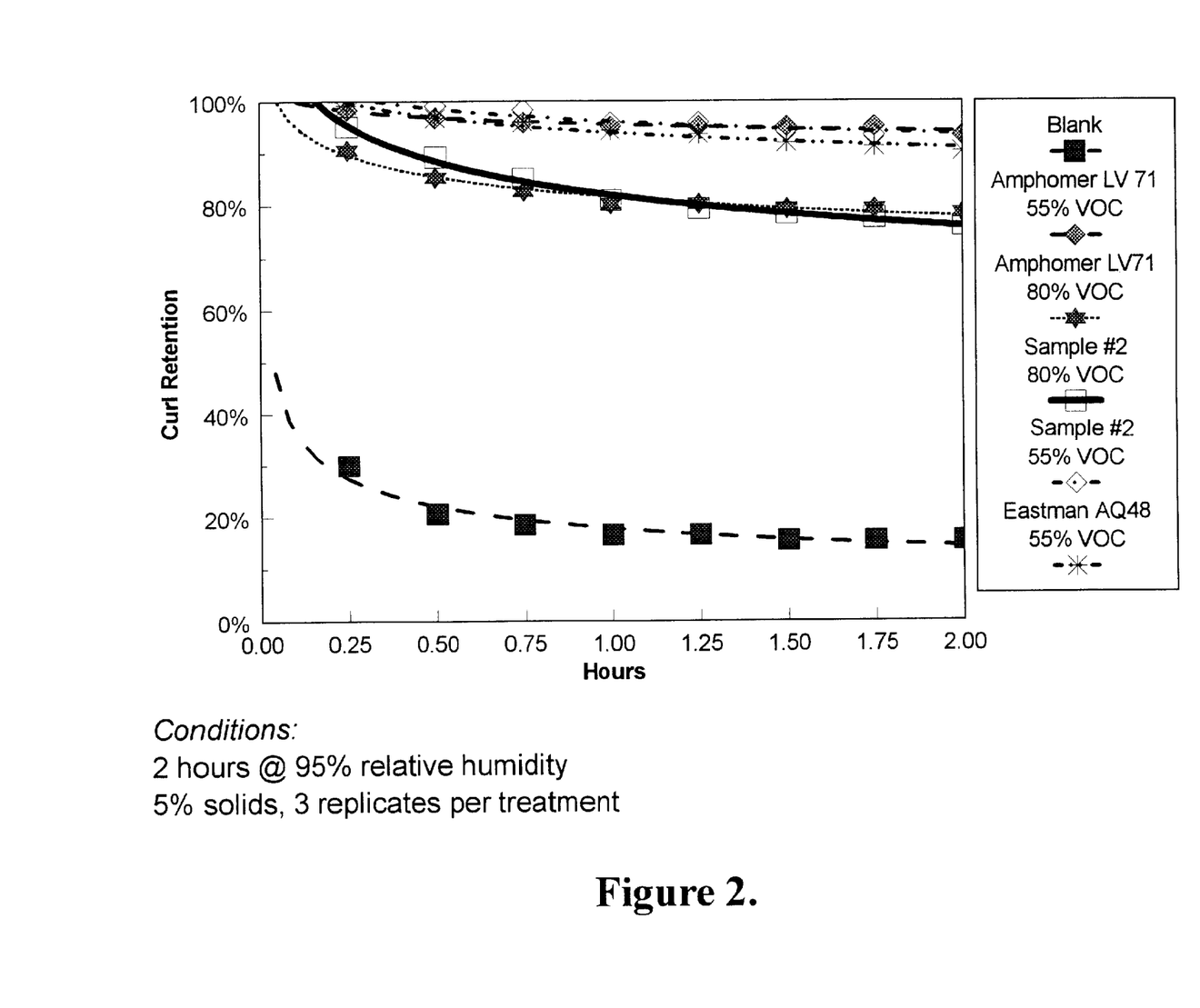
FIG. 2 illustrates curl retention of TODA-based resins (Sample #2—30/40/30 TODA/AA/MMA) in a low VOC hair spray formulation when compared to industry standards Amphomer LV71 and Eastman AQ48.
Figure 3:
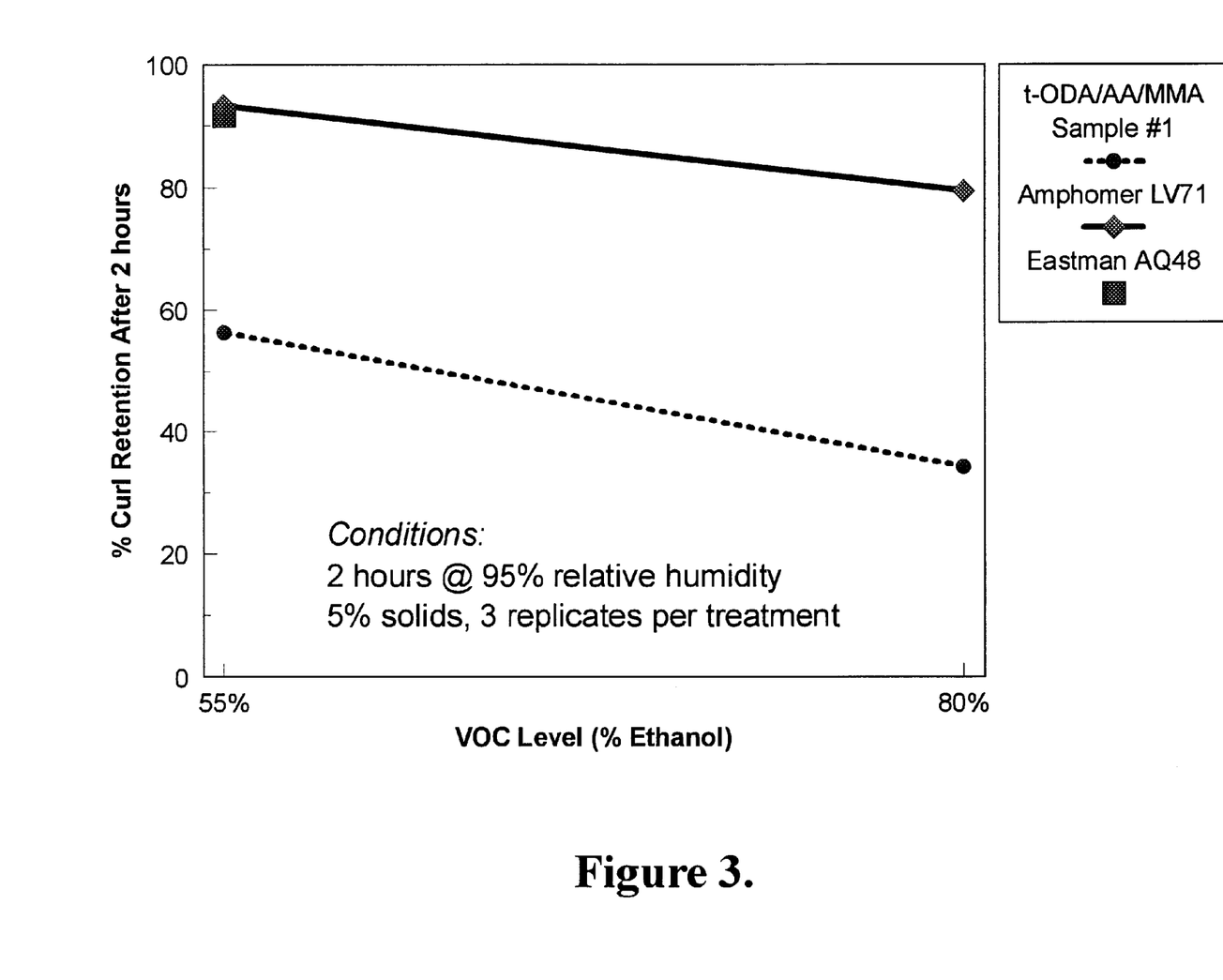
FIG. 3 illustrates the effect of VOC level (% Ethanol) on curl retention by 40/20/40 TODA/AA/MMA (Sample #1)
Figure 4:
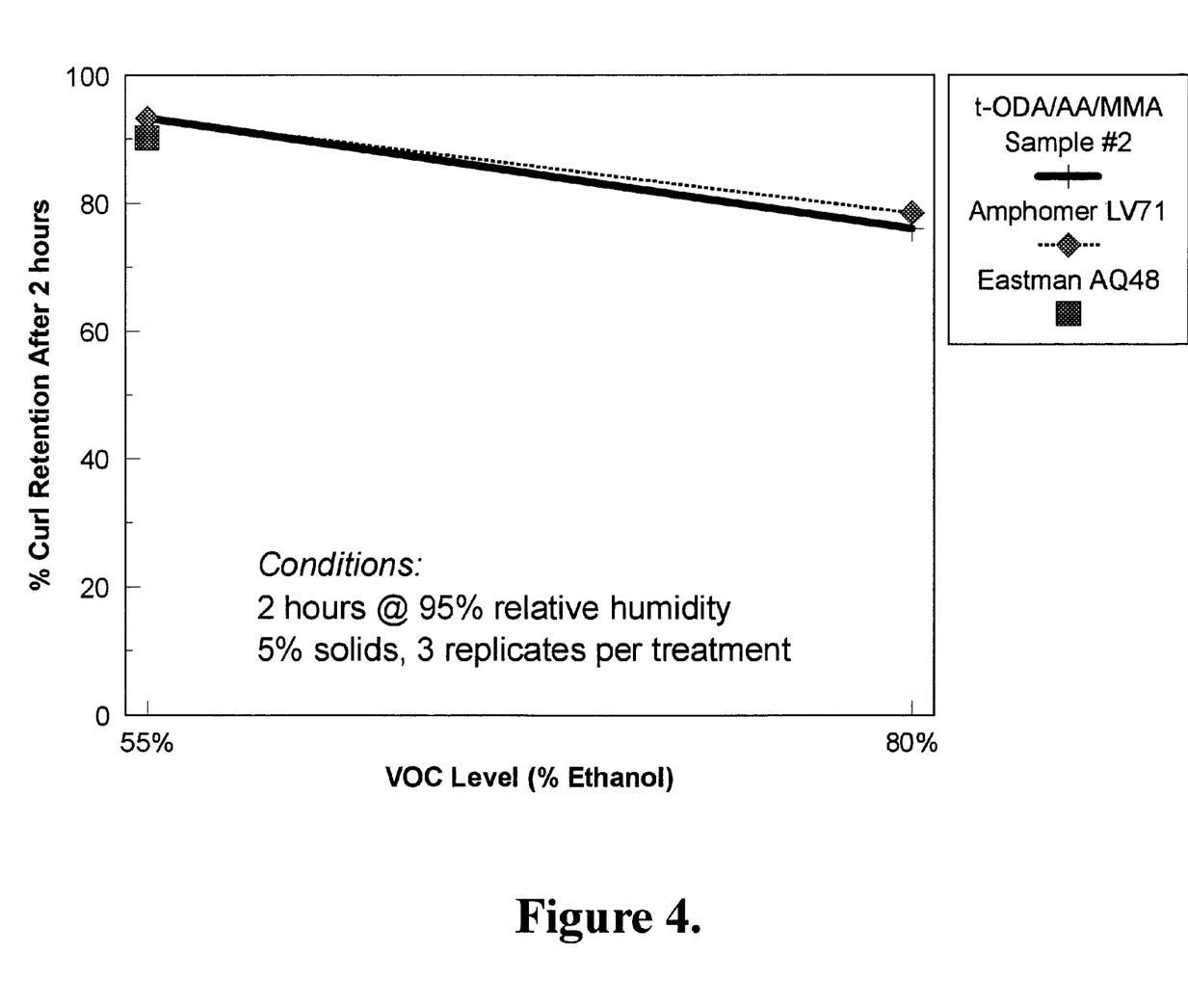
FIG. 4 illustrates the effect of VOC level (% Ethanol) curl retention by 30/40/30 TODA/AA/MMA (Sample #2).

Curl retention results are summarized in Table 4. Each chemistry sample was evaluated at 55% and 80% VOC in separate test series against 55% VOC formulas of Amphomer LV 71 and Eastman AQ 48 and 80% VOC Amphomer LV 71. Actual curl retention versus time curves are shown in FIGS. 1 and 2 for the respective samples. The data from these curves, as well as the final results in Table 4, show that while 40/20/40 TODA/AA/MMA, Sample #1, was not as ideal for curl retention, achieving only 56% and 34% retention at 55% and 80% VOC, respectively, adjusting the composition to 30140/30 TODA/AA/MMA, Sample #2, improves retention performance to 93% at 55% VOC and 76% VOC at 80% VOC. The performance of 30/40/30 TODA/AA/MMA matches those of both Amphomer LV 71 and Eastman AQ 48 at 55% VOC. FIGS. 1 and 2 show the effects of VOC level on curl retention by the resins. FIG. 4 and FIG. 4 the effect of VOC level on curl retention by 40/20/40 TODA/AA/MMA (FIG. 3) and 30/40/30 TODA/AA/MMA (FIG. 4) respectively. FIG. 4 illustrates just how closely the 30/40/30 TODA/AA/MMA parallels the performance of Amphomer LV 71 at varying VOC levels. The decrease in curl retention with increasing ethanol concentration has been noted in previous studies.

Table 4 is as follows:

TABLE 4

Curl Retention by TODA/AA/MMA Samples Compared with Amphomer LV 71 and Eastman AQ 48
2 hours @ 95% Relative Humidity
5% solids, 3 replicates per treatment

| Resin | VOC Level (% Ethanol) | % Curl Retention (after 2 hours) | Š (sample standard deviation) | 95% Confidence Interval |
|---|---|---|---|---|
| 40/20/40 TODA/AA/MMA - Sample #1 | | | | |
| Sample #1 | 55% | 56.4 | ±8.8 | ±21.8 |
| 40/20/40 TODA/AA/MMA | 80% | 34.2 | ±3.1 | ±7.7 |
| Amphomer LV 71 | 55% | 93.2 | ±1.5 | ±3.7 |
|  | 80% | 79.4 | ±5.3 | ±13.2 |
| Eastman AQ 48 | 55% | 91.7 | ±2.8 | ±6.9 |
| Blank (untreated) | —% | 11.2 | ±3.1 | ±7.6 |
| 30/40/30 TODA/AA/MMA - Sample #2 | | | | |
| Sample #2 | 55% | 93.3 | ±1.5 | ±3.7 |
| 30/40/30 TODA/AA/MMA | 80% | 76.0 | ±8.3 | ±20.5 |
| Amphomer LV 71 | 55% | 93.3 | ±5.2 | ±12.9 |
|  | 80% | 78.5 | ±9.6 | ±23.8 |
| Eastman AQ 48 | 55% | 90.2 | ±8.3 | ±20.5 |
| Blank (untreated) | —% | 15.5 | ±5.3 | ±13.1 |

By altering the composition from 40/20/40 TODA/AA/MMA to 30/40/30 TODA/AA/MMA and targeting a slightly higher molecular weight, the second sample showed a clear improvement in the target attributes. With neutralization, it was soluble in 55% and 80% ethanol solutions and mostly soluble in the aerosol concentrate and aerosol formulation. It formed a clear film on glass and performed as well as commercially available hair setting resins in curl retention testing.

While the foregoing has been set forth in considerable detail, the sequences, formulations and methods are presented for elucidation, and not limitation. Modifications and improvements, including equivalents, of the technology disclosed above which are within the purview and abilities of those in the art are included within the scope of the claims appended hereto. It will be readily apparent to those skilled in the art that numerous modifications, alterations and changes can be made with respect to the specifics of the above description without departing from the inventive concept described herein.

What is claimed is:

1. A polymer useful as a hair fixative resin, said polymer represented by the formula $$[L]_x\text{—}[M]_y\text{—}[N]_z$$

wherein

L, M and N represent a conversion unit of a monomer, at least one of said L, M and N being the conversion unit of an alkyl allyl amine monomer of formula wherein $R_1$ represents hydrogen or an alkyl substituent, $R_2$ represents hydrogen or methyl, n is an integer from 0 to 6, $R_4$, $R_5$ and $R_6$ each independently represent a hydrogen atom, an alkyl group having from 1 to 22 carbon atoms, a cycloalkyl group having from 3 to 22 carbon atoms, an aryl group having from 6 to 22 carbon atoms or an alkylaryl group having from 7 to 22 carbon atoms, and wherein at least one of $R_4$, $R_5$ and $R_6$ represents a substituent other than hydrogen and x, y and z are integers equal to or greater than 1 and a sum of x, y and z is an integer greater than 5.

2. The polymer of claim 1, wherein said alkyl ally amine is represented by the formula:

wherein $R_2$ and $R_3$ each independently represent hydrogen or methyl, l is 0 or 1, if l is 0, m is 1, and if l is 1, m is 0, n is 0 to 6

$R_4$, $R_5$ and $R_6$ each independently represent a hydrogen atom, an alkyl group having from 1 to 22 carbon atoms, a cycloalkyl group having from 3 to 22 carbon atoms, a cycloalkylene (i.e. an aryl group) having from 6 to 22 carbon atoms or an alkylaryl group having from 7 to 22 carbon atoms, and wherein at least one of said $R_4$, $R_5$ and $R_6$ represents a substituent other than hydrogen.

3. The polymer of claim 1, wherein at least one of said L, M and N is an alkyl mono allyl amine monomer.

4. The polymer of claim 1, wherein L, M and N are each independently selected from the group consisting of acrylic acid, acrylamide, methyl methacrylate, butyl aminoethyl methacrylate, methyl octyl diallyl ammonium bromide, dimethylamine ethylacrylate, tertiary-octyl acrylamide, and isobornyl methacrylate.

5. The polymer of clam 2, wherein $R_4$ and $R_6$ represent a substituent other than hydrogen; and $R_5$ is represented by the formula:

6. The polymer of claim 1, wherein said polymer is represented by the formula:

wherein l is 0 or 1, if l is 0, m is 1, and if l is 1, m is 0.

7. The polymer of claim 1, wherein said polymer is a copolymer formed from said alkyl allyl amine monomer and a methyl methacrylate monomer.

8. The polymer of claim 1, wherein said polymer is a copolymer formed from said alkyl allyl amine monomer and an acrylic acid monomer.

9. A hair spray formulation comprised of:
a volatile organic solvent at a weight percentage equal to or less than 80% of said hair spray formulation;
water;
and the polymer of claim 1.

10. The hair spray formulation of claim 9, further including acetone.

11. The hair spray formulation of claim 9 wherein said volatile organic compound is selected from the group consisting of an alcohol, dimethoxymethane, and dimethylether.

12. The hair spray formulation of claim 9, wherein said weight percentage of said volatile organic compound is equal to or less than 55% of said hair spray formulation.

13. The hair spray formulation of claim 9, wherein the polymerization product is represented by the formula:

wherein $R_2$ and $R_3$ each independently represent hydrogen or methyl, l is 0 or 1, if l is 0, m is 1, and if l is 1, m is 0, n is 0 to 6

$R_4$, $R_5$ and $R_6$ each independently represent hydrogen or an alkyl group having from 1 to 22 carbon atoms, L and N represent a conversion unit of a monomer, and x, y and z are integers equal to or greater than 1 and a sum of x, y and z is an integer greater than 5.

14. The hair spray formulation of claim 11, wherein said alkyl ally amine includes a tertiary alkyl group selected from the group consisting of a tertiary butyl group and a tertiary octyl group.

15. The hair spray formulation of claim 9, wherein said polymerizate is formed from a polymerization blend having a relative ratio of about 30:40:30 (TODA:AA:MMA).

* * * * *